United States Patent
Cai et al.

(10) Patent No.: US 10,167,479 B2
(45) Date of Patent: Jan. 1, 2019

(54) AGROBACTERIUM STRAINS FOR PLANT TRANSFORMATION

(75) Inventors: Lin Cai, Singapore (SG); Longhua Sun, Singapore (SG); Lin Fu, Singapore (SG); Lianghui Ji, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 490 days.

(21) Appl. No.: 13/513,724

(22) PCT Filed: Dec. 4, 2009

(86) PCT No.: PCT/SG2009/000470
§ 371 (c)(1),
(2), (4) Date: Jun. 4, 2012

(87) PCT Pub. No.: WO2011/068468
PCT Pub. Date: Jun. 9, 2011

(65) Prior Publication Data
US 2012/0246759 A1   Sep. 27, 2012

(51) Int. Cl.
*C12N 15/82* (2006.01)
*A01H 4/00* (2006.01)
*C07K 14/195* (2006.01)
*C12N 1/20* (2006.01)
*C12R 1/01* (2006.01)

(52) U.S. Cl.
CPC ......... *C12N 15/8205* (2013.01); *A01H 4/008* (2013.01); *C07K 14/195* (2013.01); *C12N 1/20* (2013.01); *C12R 1/01* (2013.01)

(58) Field of Classification Search
None
See application file for complete search history.

(56) References Cited

U.S. PATENT DOCUMENTS

2005/0097641 A1 * 5/2005 Wolters .............. C12N 15/8205
800/294

FOREIGN PATENT DOCUMENTS

WO   2009096900 A1   8/2009

OTHER PUBLICATIONS

McLean et al et al. Mutants of Agrobacterium VirA That Activate vir Gene Expression in the Absence of the Inducer Acetosyringone. J Biol Chem. vol. 269:2645-2651, Jan. 1994.*
McLean et al (Mutants of Agrobacterium VirA That Activate vir Gene Expression in the Absence of the Inducer Acetosyringone. J Biol Chem. vol. 269:2645-2651, Jan. 1994).*
Gelvin (Agrobacterium-mediated plant transformation: the biology behind the "gene-jockeying" tool. Microbiol Mol Biol Rev. 67:16-37, Mar. 2003).*
Jones et al (Review of methodologies and a protocol for the Agrobacterium-mediated transformation of wheat. Plant methods. 1:5, Sep. 2005).*
Wang et al (Construction of an efficient expression system for Agrobacterium tumefaciens based on the coliphage T5 promoter, Gene 242, p. 105-114, 2000).*
Collens et al (Development of auxotrophic agrobacterium tumefaciens for gene transfer in plant tissue culture. Biotechnol Prog. 20:890-896, May 2004).*
Chinese Office Action and English translation dated Feb. 5, 2013, CN Application No. 200980163391.6, Application dated Dec. 4, 2009, Applicant: Temasek Life Sciences Laboratory Limited, 13 pages.
Search Report, CN Application No. 200980163391.6, Application dated Dec. 4, 2009, Applicant: Temasek Life Sciences Laboratory Limited, 2 pages.
Jha, Timir Baran et al., "Somatic Embryogenesis in Jatropha curcas Linn., an Important Biofuel Plant," Plant Biotechnology Reports, 2007, vol. 1, pp. 135-140.
Sagi, Moshe et al., "Superoxide Production by Plant Homologues of the gp91phox NADPH Oxidase, Modulation of Activity by Calcium and by Tobacco Mosaic Virus Infection," Plant Physiology, Jul. 2001, vol. 126, pp. 1281-1290, published by Springer, © 2001 American Society of Plant Biologists.
Sujatha, M. et al., "Role of Biotechnological Interventions in the Improvement of Castor (*Ricinus communis* L.) and *Jatropha curcas* L.," Biotechnology Advances, vol. 26, No. 5, Sep. 1, 2008, pp. 424-435, Elsevier Publishing, Barking, GB.
Supplementary European Search Report, Application No. EP 09 85 1917, Place of Search: The Hague, Date of Completion: Apr. 12, 2013, 12 pages.
Blanc, G. et al, "Efficient Agrobacterium Tumefaciens-Mediated Transformation of Embryonic Calli and Regeneration of Hevea Brasiliensis Mull Arg. Plants," Plant Cell Reports, 2006, vol. 24(12), pp. 724-733.
Jayashree, R. et al., "Genetic Transformation and Regeneration of Rubber Tree (*Hevea brasiliensis* Muell. Arg.) Transgenic Plants with a Constitutive Version of an Anti-Oxidative Stress Superoxide Dismutase Gene," Plant Cell Reports, 2003, vol. 22(3), pp. 201-209.
Montoro, P. et al., "Production of Hevea Brasiliensis Transgenic Embryogenic Callus Lines by Agrobacterium Tumefaciens: Roles of Calcium," Plant Cell Reports, 2003, vol. 21(11), pp. 1095-1102.
Li, M. et al., "Establishment of an Agrobacterium-Mediated Cotyledon Disc Transformation Method for Jatropha Curcas," Plant Cell, Tissue and Organ Culture, 2008, vol. 92, pp. 173-181.

(Continued)

*Primary Examiner* — Medina A Ibrahim
*Assistant Examiner* — Wayne Zhong
(74) *Attorney, Agent, or Firm* — Rothwell, Figg, Ernst & Manbeck, P.C.

(57) ABSTRACT

The present invention relates to the field of the production of transgenic plants through *Agrobacterium*-mediated transformation of cells of somatic embryogenic calli or embryogenic suspension cultures and regeneration of the transformed cells into fruit-setting plants. In particular, the present invention relates to the production of transgenic plants in the Euphorbiaceae family. The present invention further relates to media compositions, selection methods and engineered *Agrobacterium tumefaciens* strains that improve *Agrobacterium*-mediated transformation efficiency.

2 Claims, 9 Drawing Sheets

(56) References Cited

OTHER PUBLICATIONS

Sobha, S. et al., "Genetic Transformation of Hevea Brasiliensis with the Gene Coding for Superoxide Dismutase with FMV 34S Promoter," Current Science, 2003, vol. 85(12), pp. 1767-1773.

Venkatachalam, P. et al., "Rubber Tree (*Hevea brasiliensis* Muell. Arg.)," Methods in Molecular Biology, 2006, vol. 344, pp. 153-164.

He, Y. et al., "Agrobacterium Tumefaciens-Mediated Transformation of Jatropha Curcas: Factors Affecting Transient Transformation Efficiency and Morphology Analysis of Transgenic Calli," Silvae Genetica, Dec. 3, 2009, vol. 58 (3), pp. 123-128.

Arokiaraj, P. et al., "Agrobacterium-Mediated Transformation of Hevea Anther Calli and Their Regeneration into Plantlets," Journal of Natural Rubber Research, 1996, vol. 11(2), pp. 77-87.

Bulgakov, V.P. et al., "Effects of Ca(2+) Channel Blockers and Protein Kinase/Phosphatase Inhibitors on Growth and Anthraquinone Production in Rubia Cordifolia Callus Cultures Transformed by the rolB and rolC Genes," Planta, 2003, vol. 217(3), pp. 349-355.

Sepulveda-Jimenez, G. et al., "Betacyanin Synthesis in Red Beet (*Beta vularis*) Leaves Induced by Wounding and Bacterial Infiltration is Preceded by an Oxidative Burst," Physiological and Molecular Plant Pathology, 2004, vol. 64(3), pp. 125-133.

Sepulveda-Jimenez, G. et al., "A Red Beet (*Beta vulgaris*) UDP-Glucosyltransferase Gene Induced by Wounding, Bacterial Infiltration and Oxidative Stress," Journal of Experimental Botany, 2005, vol. 56(412), pp. 605-611.

International Search Report, PCT/SG2009/000470, International Filing Date: Dec. 4, 2009, Applicant: Temasek Life Science Laboratory Limited, 5 pages.

* cited by examiner

| Strain | AGL1 | AGL1 | AGL2 |
|---|---|---|---|
| Vector | none | pCambia1305.1 | pCambia1305.1 |

| AS (uM) | 200 | 0 | 200 | 0 | 200 |

A.  B.  C.

AGROBACTERIUM STRAINS FOR PLANT TRANSFORMATION

CROSS-REFERENCE TO RELATED APPLICATION

The present application is a national stage filing under 35 U.S.C. § 371 of PCT/SG2009/000470, filed on 4 Dec. 2009, which application is incorporated herein by reference.

BACKGROUND OF THE INVENTION

The present invention relates to the field of the production of transgenic plants through *Agrobacterium*-mediated transformation of cells of somatic embryogenic calli or embryogenic suspension cultures and regeneration of the transformed cells into fruit-setting plants. In particular, the present invention relates to the production of transgenic plants in the Euphorbiaceae family. The present invention further relates to media compositions, selection methods and engineered *Agrobacterium tumefaciens* strains that improve *Agrobacterium*-mediated transformation efficiency.

The publications and other materials used herein to illuminate the background of the invention or provide additional details respecting the practice, are incorporated by reference, and for convenience are respectively grouped in the Bibliography.

The world is facing dwindling supply is fossil fuel and worsening Green House Effect. There is an urgent demand to increase production and consumption of renewable energy. Biofuels have been recognized as a national priority for many countries in their search for alternative sources to meet their energy security needs and at the same time help reduce $CO_2$ emissions that cause the Green House Effect. The demand for biofuel has put increasing pressure on food production. For example, to satisfy the biofuel need for Germany in 2017 as mandated by the German government the entire farm land of this country would have to be used for growing bioenergy crops with no land left for food production. To ease this competition for land and to satisfy our need for renewable fuels, there is a strong need to utilize marginal land for bio-energy production.

Euphorbiaceae family includes valuable trees species such as rubber (*Hevea brasiliensis*) and *Jatropha curcas* and castor oil plant (*Ricinus communis*). Several unique characteristics of *Jatropha curcas* make it an ideal plant for biodiesel production. These characteristics include the ability to grow on marginal land; low requirement for water; a non-food crop status; fast oil production in 0.5-2 years after planting compared to more than 3.5 years for oil palm. Accordingly, the Indonesian government has announced that they will dedicate about 3 million hectares of land for *jatropha* planting in the next 5 years. Many other Asian countries are adopting similarly bold plans. Amongst the various countries, India is the most advanced in terms of establishment of *Jatropha* plantations. However, the seed yield of an Indian *Jatropha* plantation remains low, ranging from 0.4 to 12 MT/Ha (compared with about 19Mt/Ha for palm fruit). Similarly, the reported kernel oil contents varied wildly from 40.4-85.3% (Sun, W. B., *Jatropha* International Congress 2008, Singapore). Castor oil is an important source of lubricant and is also a potential source of biodiesel in the future.

This difference is at least in part attributed to the lack of research in breeding and farm management in *Jatropha curcas*. Genetic engineering is recognized as a fast method for crop improvement. Plant transformation is essentially a two step process, i.e., delivery of genes into a host cell followed by regeneration of the transformed cell into a plant. Somatic embryogenic calli or somatic embryogenic suspension cultures is generally regarded as the most efficient method of regeneration as most of the transformed cells have already acquired the embryogenic potential that will drive them to develop into a somatic embryo quite spontaneously. An efficient method for initiation of *Jatropha* somatic embryos and maintenance of embryogenic suspension cultures have been described (International patent application No. PCT/SG2009/000015; US Provisional Patent: 61/025,430).

Plant transformation methods may be broadly classified into two groups: Direct DNA transfer, such as electroporation and particle bombardment, and *Agrobacterium*-mediated transformation. To date, the later has become method of choice in transformation of many plants. In fact, most commercially available transgenic varieties of cotton and rapeseed derived from this method (Cerdeira and Duke, 2006; Dunwell, 2000). Previous work in maize (Dunwell, 1999; Vega et al., 2008; Wang and Frame, 2009), rice (Christou, 1997; Hayashimoto et al., 1990; Lee et al., 1991; Zhang et al., 1997) and soybean (Christou et al., 1988; Christou et al., 1987; Olhoft et al., 2003) demonstrate different examples of different methods for introduction of foreign DNA into crop plants. Transgenic plants may be obtained following *Agrobacterium*-mediated transformation of the. This method is characterized by a low frequency of transgenic production and by the formation of chimeras (Gould et al., 1991). Transgenic plants may also be obtained following *Agrobacterium*-mediated transformation of immature embryos. Immature embryos have been the choicest explant to date since there is usually a very high frequency of callus induction and plant regeneration from immature embryos. Following transformation, immature embryos, regardless of the method of DNA delivery, are very hard to regenerate into fertile plants (Cheng et al., 1997). In addition, it is usually very difficult to obtain immature embryos throughout the year, and their suitable stage for culture is also strictly time dependent, thus limiting their use. While the frequency of transformation with immature embryos ranges from about 0.14 to about 4.3%, the number of transgenics recovered is a small fraction of the number of embryos transformed (Cheng et al., 1997). Somatic embryos are suitable for transformation via *Agrobacterium tumefaciens* and particle bombardment (Christou, 1997; Sidorov and Duncan, 2009). Somatic embryogenic calli can be maintained conveniently as a liquid culture and fast-amplified for production of clonal populations. Thus, once a somatic embryogenic culture of an elite variety of established, it will save years of time developing genetically pure lines that are stacked with transgenic traits.

Many different explants can be co-cultured with an *Agrobacterium* strain harboring a T-DNA vector to produce a transgenic cell, which can be regenerated into a normal plant through somatic embryogenesis or organogenesis pathway. Research on regeneration and transformation of *Jatropha curcas* has been very limited.

Jha et al. (2007) reported production of somatic embryos of *Jatropha curcas* using leaf tissues. (Li et al., 2008) report transformation of *Jatropha curcas* by co-culturing leaf disc with *Agrobacterium* and regenerate via organogenesis pathway. However, both methods are not easily repeatable in the Jatropha research community (Z. Mao et al., Temasek Life Sciences Laboratories, Singapore, peronsonal communication; A. Suwanto, Bogor Agricultural University, Indonesia; personal communication).

Mao et al. (U.S. provisional patent application No. 61/122,454) discloses production of transgenic *Jatropha curcas* plants by *Agrobacterium*-mediated transformation of leaf explants and regeneration via somatic embryogenesis pathway. The invention also used grafting technique to overcome rooting difficulties of the transgenic plantlets.

International Publication No. WO 2008/012832 discloses an efficient process for in vitro propagation of Jatropha through direct regeneration of leaf disc without any intermediary callus phase. Genetic transformation based on this regeneration method has not been reported.

Thus, a reliable and efficient method for transformation of Jatropha is yet to be developed. Improvements that would lead to shorter regeneration time, higher transformation rate and high throughput transformation work are particularly welcome.

Delivery of T-DNA by *Agrobacterium* cells into plant host cells depends on pre-induction of virulence genes. Known inducers that are naturally produced in wounded plant tissues include a variety of phenolic compounds such as acetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde) (U.S. Pat. No. 6,483,013).

A constitutively expressed virG mutant protein (virGN54D) has been found to enhance *Agrobacterium* virulence and transformation efficiency (Hansen et al., 1994). Similarly, supplementation of virulence inducers, e.g., acetosyringone or nopaline, increased transformation efficiency of cotton shoot tips (Veluthambi et al., 1989) and somatic embryogenic callus that was propagated on solid media (U.S. Pat. No. 6,483,013). Acetosyringone is indispensable for transformation of a large number of fungi, which are unable to secrete *Agrobacterium* virulence inducing compounds (Bundock et al., 1995; de Groot et al., 1998).

U.S. Pat. Nos. 6,162,965 and 6,310,273 disclose that *Agrobacterium tumefaciens* induces necrosis during co-culture with plant cells, particularly of the Gramineae. Compounds that inhibit necrosis, e.g., 2,5-norbornadiene, norbornene, silver thiosulfate, aminoethoxyvinylglycine, cobalt salts, acetyl salicylic acid, or salicylic acid, may be used to improve transformation efficiency. Similarly, a nucleotide sequence that encodes a cell death suppressor protein (p35, iap or dad-1) may be included in the transformation vector to achieve the same goal.

Similarly, wounding and *A. tumefaciens* infection of soybean cotyledonary node explants result in extensive enzymatic browning and cell death in the tissue. Thiol compounds, such as L-cysteine, dithiothreitol (DTT), and sodium thiosulfate, improves T-DNA delivery by inhibiting the activity of plant pathogen and wound-response enzymes, such as peroxidases (PODs) and polyphenol oxidases (PPOs). Additive effect was observed with the thiol compounds. The most effective combination for soybean is 1 mM Na-thiolsulfate+8.8 mM L-cysteine+1 mM DTT (Olhoft et al., 2003).

Nitric oxide (NO) has been implicated in defense responses and its control or elimination may increase pathogen infection such as that of *Agrobacterium* during plant transformation (U.S. Pat. No. 7,388,126). NO modulators include of NG-monomethyl-L-arginine, monoacetate salt (N-Me-L-Arg, AcOH; L-NMMA), NG-monomethyl-L-homoarginine, monoacetate salt (NMMHA, AcOH), NG-monoethyl-L-arginine, monoacetate salt (NMEA, AcOH), NG-monomethyl-L-arginine, di-p-hydroxyazobenzene-p"-sulfonate salt (N-Me-L-Arg, diHABS; L-NMMA), and clinorotation.

Activation of plasma membrane NADPH oxidase is associated with the incompatible interaction of plants with microbes, leading to production of superoxide, which can be converted into $H_2O_2$ by superoxide dismutases. NADPH oxidase can be effectively inhibited by diphenylene iodonium (Sagi and Fluhr, 2001). To date, there is no evidence to suggest that NADPH oxidase plays any role in compatible plant-microbe interactions, such as jatropha-*agrobacterium* interaction during transformation process. Neither exist any report on the use of NADPH oxidase inhibitors, such as diphenylene iodonium, to improve *Agrobacterium*-mediated plant transformation efficiency.

Overgrowth of *Agrobacterium* jeopardizes the survival of the transformed plant cells and also has an effect on the T-DNA transfer process. Insertion of multiple copies of a gene of interest into a plant cell is influenced by the frequency of T-DNA transfer into the cell. *Agrobacterium*-mediated transformation protocols strive to attain transformation events with a limited number of copies of DNA entering into any one cell. The presence of multiple inserts can lead to gene silencing or reduce expression levels of transformed genes, which is caused by several mechanisms including recombination between the multiple copies.

International Publication No. WO 2001/09302 and U.S. Patent Application Publication 2003/0204875 discloses control of *Agrobacterium* growth during the transformation process in order to improve transformation efficiency. The use of inhibiting agents during inoculation and co-culture of *Agrobacterium* with a transformable plant cell results, according to the disclosure, in increased transformation efficiencies and a low copy number of an introduced genetic component in several plant systems. Preferred growth-inhibiting agents are compounds containing heavy metals such as silver nitrate or silver thiosulfate, antibiotics such as carbenicillin, and a combination of antibiotics and a clavulanic acid such as augmentin or timentin.

U.S. Pat. No. 6,323,396 claims a process to produce a dicotyledonous transgenic plant by systemically infecting auxotrophic *Agrobacterium* strain with explant tissue, protoplast or microspore and regeneration on a plant regeneration medium, in the absence of a compound with a bacteriocidal or bacteriostatic effect on the auxotrophic *Agrobacterium* strain. The *Agrobacterium* strain is LBA4404metHV (LMG P-18486) or ATHV ade, his, (LMG P-18485). International Publication No. WO/2005/103271 discloses improved method for *Agrobacterium* mediated transformation of embryogenic suspension culture which is achieved by the use of solid support for co-culturing of the embryogenic cells and a set of media for co-culture and selection of transformants. The method is particularly suitable for transformation of cotton embryogenic calli.

SUMMARY OF THE INVENTION

The present invention relates to the field of the production of transgenic plants through *Agrobacterium*-mediated transformation of cells of somatic embryogenic calli or embryogenic suspension cultures and regeneration of the transformed cells into fruit-setting plants. In particular, the present invention relates to the production of transgenic plants in the Euphorbiaceae family. The present invention further relates to media compositions, selection methods and engineered *Agrobacterium tumefaciens* strains that improve *Agrobacterium*-mediated transformation efficiency.

In particular this invention relates to method for preparation of somatic embryogenic calli that are highly competent for T-DNA conjugation by agrobacterial cells; medium compositions and co-culture conditions for *Agrobacterium*-mediated transformation and cell line maintenance; method for selection for transgenic cells that are prone to killing by *Agrobacterium* due to over-growth and antibiotic resistance of the agrobacterial cells, and regeneration of the transformed cells into fruit-setting plants.

Thus in a first aspect, the present invention provides method for the transformation of plants of the Euphorbiaceae family. The method comprises the steps of:

(a) establishing and maintaining cells of embryogenic calli;

(b) co-culturing the cells with a culture of *Agrobacterium* harboring a T-DNA vector of interest containing a polynucleotide of interest to produce transformed cells having the polynucleotide of interest stably incorporated into their genome in a co-culture medium;

(c) selecting the transformed cells on a selection medium;

(d) developing the selected transformed cells into transgenic somatic embryos on a development medium;

(e) maturing the transgenic somatic embryos on a maturation medium;

(f) germinating the somatic embryos into plantlets on a germination medium; and (g) transferring the plantlets to soil to further develop into flowering plants.

In one embodiment, the present invention relates to method for preparation of somatic embryogenic calli that are highly competent for T-DNA conjugation by Agrobacterial cells. In one embodiment, the embryogenic calli are derived from somatic embryos. In another embodiment, the embryogenic calli are derived from zygotic embryos. In one embodiment, the calli are subcultured regularly, preferably about every week, by transferring part of the cell mass to about 20 ml to about 100 ml liquid medium in a suitable container. Freshly subcultured calli that are about 2 days to about 7 days after subculture are preferred for transformation. In one embodiment, a preferred liquid medium contains modified MS salts (MS salts without $NH_4NO_3$), MS vitamins, about 10 g/l to about 30 g/l sucrose, about 10 g/l to about 80 g/l polyethylene glycol (PEG) 8000, about 0.01 mg/l to about 2 mg/l 2,4-dichlorophenoxyacetic acid (2,4-D), about 0.1 g/l to about 1 g/l glutamine and about 0.1 g/l to about 1 g/l asparagine. Alternatively, solidified media or filter-supported medium containing the media components may be used to propagate embryogenic calli.

In another embodiment, the present invention relates to a medium composition for efficient delivery of T-DNA into embryogenic calli. In one embodiment, the medium contains an inhibitor of NADPH oxidase, such as diphenylene iodonium (DPI) in the range between about 1 μM and about 50 μM. In one embodiment, the medium is preferably supplemented with an inducer of the *Agrobacterium* virulence, such as acetylsyringone (AS) in the range between about 5 μM and about 500 μM. In another embodiment, the medium contains the *Agrobacterium* MinAB salts (Chilton et al., 1974). In a further embodiment, the medium contains low concentration of glucose, in the range between about 5 mM and about 50 mM. In an additional embodiment, the medium contains glycerol, in the range between about 0.1% and about 2%. In a further embodiment, the medium optionally contains a compound, such as histidine, that supports normal growth of Agrobacterial cells.

In another embodiment, the present invention relates to use of a preferred *Agrobacterium* strain (AGL2). In accordance with this embodiment the *Agrobacterium* strain contains a constitutively active virA gene. In one embodiment, the strain needs no chemical inducers for activation of virulence. In another embodiment the virA gene is integrated into the genome or Ti plasmid for improved stability. In a further embodiment, the virA gene is derived from a supervirulent strain. In an additional embodiment, the virA gene is derived from AGL1. In one embodiment, the strain does not contain a wild type allele of virA. In another embodiment, the use of the strain improves transformation efficiency.

In another embodiment, the present invention relates to use of a preferred *Agrobacterium* strain (AGL3). In one embodiment, the strain further contains a mutation that suppresses growth of *Agrobacterium* cells in selection media. In another embodiment, the strain contains a mutation affecting amino acid utilization, which preferably does not affect utilization of glutamine or asparagine. In a further embodiment, the mutation is in the a background with a constitutively active virA allele. In another embodiment, the use of the strain improves transformation efficiency.

In another embodiment, the present invention relates to use of a medium-over-lay technique for selection of transformants. In one embodiment, the technique improves control of over-growth of *Agrobacterium*. In another embodiment the medium contains a compound that inhibits growth of *Agrobacterium* cells. In a further embodiment, the said medium further contains a selection agent that inhibits growth of non-transformed plant cells.

In another embodiment, the present invention relates to an improved method for selection of transformed cells and regeneration of the transformed cells into normal plants. In one embodiment, the method includes a liquid stage. In another embodiment, the liquid stage shortens the regeneration time. In a further embodiment, the liquid stage is immediately or shortly after co-culture with an *Agrobacterium* strain. In an additional embodiment, the strain is preferably one which is not able to utilize at least one amino acid. In another embodiment, the liquid medium contains an inhibitor of *Agrobacterium* growth, such as cefotaxime, carbenicillin, timentin and the like, and a selecting agent for transformed plants cells, such as a plant active antibiotic or herbicide.

BRIEF DESCRIPTION OF THE FIGURES

FIG. 6A: Somatic embryogenic calli were co-cultured with AGL2(pCambia1305.1) and selection was done in embedded in LMP Bd2 medium as described in Example 2. FIG. 6B: One of the plants of FIG. 6A was stained with X-gluc. FIG. 6C: Examples of transgenic plants in soil pots 7 months after co-culture.

FIG. 9A: *Jatropha curcas* somatic embryogenic calli was co-cultured with AGL3(pCambia1305.1) for 2.5 day and selection was done in J20P medium with 7 mg/l hygromycin and 300 mg/l cefotaxime for two weeks. Subculture was done in a similar medium with reduced sucrose (10 g/l) for another 2 weeks. FIG. 9B: The same co-cultured calli selected on solid B2d medium with 7 mg/l hygromycin and 300 mg/l cefotaxime for 4 weeks. FIG. 9C: The same co-cultured calli with selection done in embedded LMP B2d medium for 4 weeks.

DETAILED DESCRIPTION OF THE INVENTION

Figure 1:
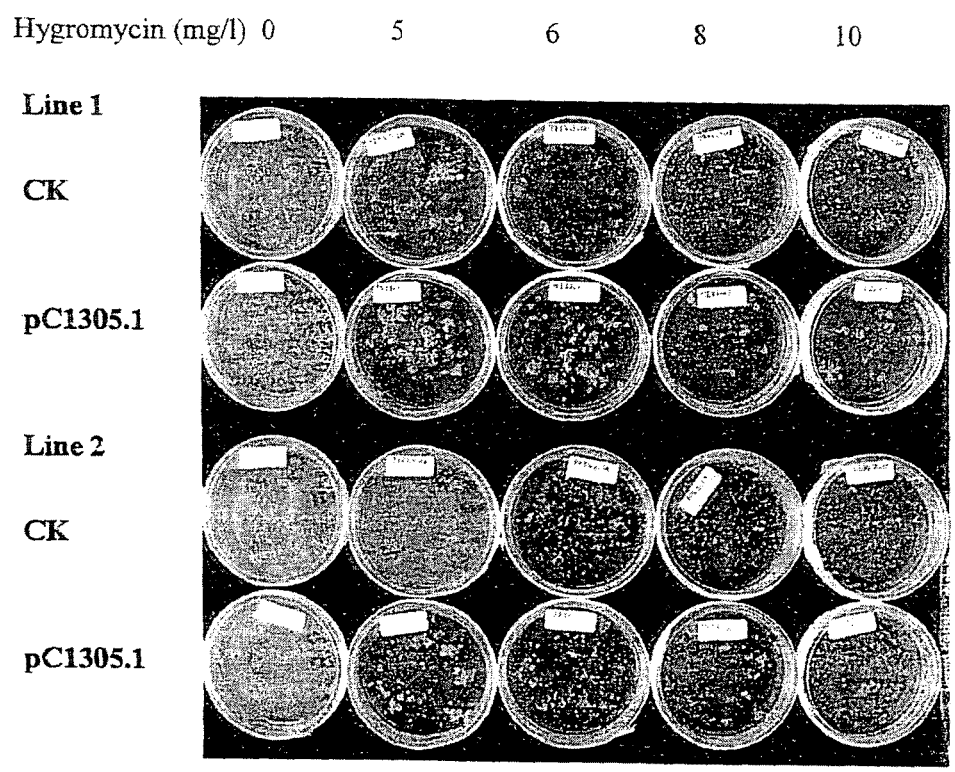
FIG. 1 shows suspension culture that has been transformed by AGL2(pC1305.1). Embryos were stained with x-gluc (5-bromo-4-chloro-3-indolyl beta-D-glucuronide) 2 months after co-culture.

The present invention relates to the field of the production of transgenic plants through *Agrobacterium*-mediated transformation of cells of somatic embryogenic calli or embryogenic suspension cultures and regeneration of the transformed cells into fruit-setting plants. In particular, the present invention relates to the production of transgenic plants in the Euphorbiaceae family. The present invention further relates to media compositions, selection methods and engineered *Agrobacterium tumefaciens* strains that improve *Agrobacterium*-mediated transformation efficiency.

Thus in a first aspect, the present invention provides method for the transformation of plants of the Euphorbiaceae family. The method comprises the steps of:

(a) establishing and subculturing cells of embryogenic calli;

(b) co-culturing freshly subcultured cells with a culture of *Agrobacterium* harboring a T-DNA vector of interest containing a polynucleotide of interest to produce transformed cells having the polynucleotide of interest stably incorporated into their genome in a co-culture medium;

(c) selecting the transformed cells on a selection medium;

(d) developing the selected transformed cells into transgenic somatic embryos on a development medium;

(e) maturing the transgenic somatic embryos on a maturation medium;

(f) germinating the somatic embryos into plantlets on a germination medium; and (g) transferring the plantlets to soil to further develop into flowering plants.

In one embodiment, the cells for co-culturing are derived from the Euphorbiaceae family. In another embodiment, the cells are derived from the Jatropha genera. In one embodiment, the embryogenic calli are derived from somatic embryos. In another embodiment, the embryogenic calli are derived from zygotic embryos. In a preferred embodiment, the cells are derived from somatic embryogenic calli. In one embodiment, these cells are cultured on a solid medium. In another embodiment, the cells are cultured in a liquid medium. Any medium that is suitable for maintaining cells with high embryogenecity can be used. It has been found that a medium that contains modified MS salts, MS vitamins, a carbohydrate source, such as sucrose, polyethylene glycol (PEG), an auxin, such as 2,4-dichlorophenoxyacetic acid (2,4-D), glutamine and asparagine is particularly suitable. In one embodiment, the medium comprises modified MS salts (MS salts without $NH_4NO_3$), MS vitamins, about 10 g/l to about 30 g/l sucrose, about 10 g/l to about 80 g/l PEG 8000, about 0.01 mg/l to about 2 mg/l 2,4-D, about 0.1 g/l to about 1 g/l glutamine and about 0.1 g/l to about 1 g/l asparagine is particularly suitable and is a preferred medium. The cells are subcultured regularly, preferably about every week. In one embodiment, the cells are cultured in a condition with 2000-3000 lux lighting with 16/8 day/night cycles, 26° C.-30° C. and gentle shaking at 50-100 rpm.

In one embodiment, a method is provided for preparing somatic embryo genic calli that are highly competent for T-DNA conjugation by Agrobacterial cells. In one embodiment, the embryogenic calli are subcultured regularly, preferably about every week, by transferring part of the cell mass to about 20 ml to about 100 ml liquid medium in a suitable container. As a variation, solidified media or filter-supported medium containing the media components may be used as the cell culture medium. Freshly subcultured calli that are about 2 days to about 7 days after subculture are preferred for transformation.

In another embodiment, the present invention relates to a co-culture medium composition for efficient delivery of T-DNA into embryogenic calli. In one embodiment the medium is one that favors induction of virulence of Agrobacterial cells, such as a medium that contains the *Agrobacterium* MinAB salts (Chilton et al., 1974). In one embodiment, the medium also contains vitamins, such as B5 vitamins. In another embodiment, the medium also contains an inhibitor of NADPH oxidase, such as diphenylene iodonium (DPI) in the range between about 1 μM and about 50 μM. The use of an inhibitor of NAPDH oxidase leads to an improved plant transformation efficiency. In one embodiment, the medium is preferably supplemented with an inducer of the *Agrobacterium* virulence, such as acetylsyringone (AS) in the range between about 5 μM and about 500 μM. Other known inducers include sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde). In a further embodiment, the medium optionally contains a compound, such as histidine, that supports normal growth of Agrobacterial cells. In one embodiment, the medium contains a low concentration of glucose, in the range between about 5 mM and about 50 mM. In an additional embodiment, the medium contains glycerol, in the range between about 0.1% and about 2% and a buffering agent, such as 2-[N-morpholino]ethanesulfonic acid (MES), in a range between about 1 mM to about 20 mM and adjusted about pH 5.7.

In one embodiment, *Agrobacterium* that are pre-induced are used in the co-culture step. In another embodiment, the *Agrobacterium* is a supervirulent strain, such as *Agrobacterium tumefaciens* strain AGL1. In a further embodiment, the *Agrobacterium* contains a mutant virA protein that needs no added inducer for acquisition of virulence. In one embodiment, the *Agrobacterium* containing a mutant virA protein is *A. tumefaciens* strain AGL2. In another embodiment, the *Agrobacterium* is an auxotrophic strain, such as *A. tumefaciens* strain AGL3. In one embodiment, the auxotrophic strain is not auxotrophic to glutamine and asparagine.

The cells with high somatic embryogenesis potential are co-cultured with *Agrobacterium* containing a T-DNA vector containing a polynucleotide of interest to produce transformed cells having the polynucleotide of interest stably integrated into their genome. The *Agrobacterium* typically also contains a selectable marker gene, such as described herein. In one embodiment, the co-culturing is performed on as solid medium. In another embodiment, the co-culturing is preferably performed on a porous support, such as a porous membrane or filter paper. The porous support may be soaked in liquid, medium, may be overlaid on a solid medium or may be overlaid on a liquid medium. Co-culture is performed in an environment with about 1000 lux constant lighting. 24° C.-25° C. for 2-4 days.

The transformed cells are selected by culturing them on a selection medium. In one embodiment, the selection is performed on a solid medium. In a preferred embodiment, the selection is performed by embedding the co-cultured plant cells in a solid medium. In another preferred embodiment, the selection is performed in a liquid medium. Any suitable medium may be used for selecting transformed cells. In one embodiment, the selection medium comprises Gamborg B5 salts and B5 vitamins. The selection medium further contains a carbohydrate source, such as sucrose, an auxin, such as 2,4-D. In one embodiment, the medium comprises Gamborg B5 salts and B5 vitamins, about 10 to about 30 g/l sucrose, and about 0.1 mg/l to about 10 mg/l 2,4-D, preferably about 2 mg/l 2,4-D. The medium may be solidified using typical solidifying agents such as phytagel, agar and low melting point (LMP) agarose. The selection medium also contains a compound for selection of transformed cells (selection agent) and is dependent on the selectable marker gene that is included in the *Agrobacterium*. Examples of compounds that can be used include plant active antibiotics or herbicides. The selection medium also preferably contains a compound that suppresses the growth of agrobacterial cells. Such compounds are well known in the art and include cefotaxime, carbenicillin, and timentin.

In one embodiment, the selection of transformed cells is done in condition with 25° C.-30° C. temperature, preferably about 26° C. and with 1.6 hours lighting per day and under one 36 W (about 2000 lux) warm-light tube. Subculturing can be done in the same fresh medium every 2-3 weeks. Calli resistant to the selecting agent are transferred to a hormone-free medium supplemented with glutamine and asparagine and further supplemented with a selection agent, such as hygromycin, and an *Agrobacterium* inhibiting compound, such as cefotaxime. An example of such a medium is the DGA medium described herein, which contains $NH_4NO_3$-free MS salt, Gamborg B5 vitamins, 30 g/l sucrose, 2.4 g/l phytagel, 1 g/l glutamine, 0.5 g/l asparagine, pH 5.8. Once green cotyledonary stage embryos are produced, they can be transferred to an embryo maturation medium for 2-4 weeks. An example of a suitable embryo maturation medium is the M9-2 medium described herein, which contains $NH_4NO_3$-free MS salts, Gamborg B5 vitamins, 20 g/l sucrose, 20 g/l maltose, 1 g/l glutamine, 0.5 g/l asparagine, 2.4 g/l phytagel, 0.1 g/l casein hydrolysate, pH 5.8, and supplemented with a selection agent and a *Agrobacterium* inhibiting agent. Germination of fully developed embryos is well known in the art. An example of a suitable germination medium is the G35-2 medium described herein, which contains MS salts, vitamins, 20 g/l sucrose, 5.5 g/l agar, 0.1 g/l casein hydrolysate, 2 mg/l gibberellic acid ($GA_3$), pH 5.8. Germinated embryos with roots are further developed in a medium with low concentration of auxin, such as α-naphthaleneacetic acid (NAA) at about 0.01 mg/l. An example of such a medium is the W9 medium described herein, which contains MS vitamins, 20 g/l sucrose, 1 mg/l $FeSO_4$, 0.1 g/l casein hydrolysate, 0.01 mg/l NAA, 5.5 g/l agar, pH 5.8. Activated charcoal at about 0.1 g/l to about 0.5 may be included in the medium to improve growth of small plants. Another example of such a medium is the W15 medium described herein, which contains ½ MS salts, ½ MS vitamins, 15 g/l sucrose, 1 mg/l $FeSO_4$, 0.1 activated charcoal, 0.1 g/l casein hydrolysate, 0.01 mg/l NAA, 5.5 g/l agar, pH 5.8.

Selection for transformed cells by the medium embedding method is performed by spreading thoroughly washed co-cultured somatic embryogenic calli, at about 0.1 g per 90 mm Petri dish, on a solid medium, such as Bd2 medium described herein that contains Gamborg B5 salts, B5 vitamins, 30 g/l sucrose, 2.2 g/l phytagel, 2 mg/l 2,4-D sodium salt, pH5.8, and supplemented with selection agent and a *Agrobacterium* inhibiting agent. About 10 ml low melting point (LMP) agarose (0.6%) containing Bd2 medium (after cooled down to about 40° C.) supplemented with the same selection agent was over-laid the calli. Subculture was done by carefully picking up resistant calli, placing on a fresh Bd2 medium and overlayed with LMP Bd2 medium. Selection in the LMP medium is done for 8-10 weeks until cotyledonary stage embryos are produced. Resistant embryos at around torpedo to cotylendonary stages are transferred to DGA medium supplemented with a selection agent. In about 3-4 weeks, small green cotyledonary stage embryos are transferred to M9-2 medium supplemented with a selection agent. In about 3-4 weeks, the embryos are transferred to G35-2 medium as described herein containing a selection agent. At this stage, up to four 36 W light tubes may be used. Lighting remains 16 hr per day. In about 3 weeks, germinated embryos are transferred to W9 medium containing a selection agent. In about 2-3 weeks, the plantlets are transferred to W15 medium (without hygromycin). Rooted plantlets are ready for planting in soil in 2-3 weeks.

Selection of transformed cells in liquid medium can be done in any suitable medium for a period of time sufficient to produce transgenic torpedo or cotyledonary stage somatic embryos. In one embodiment, the liquid selection medium comprises Gamborg B5 salts and B5 vitamins. The selection medium further contain a carbohydrate source, such as sucrose, an auxin, such as 2,4-D. In one embodiment, the medium comprises Gamborg B5 salts and B5 vitamins, about 10 to about 20 g/l sucrose, and about 0.1 mg/l to about 10 mg/l 2,4-D, preferably about 2 mg/l 2,4-D. In one embodiment, the amount of the carbohydrate source, such as sucrose, is reduced in each subculture from a high of about 20 to a low of about 10 g/l. The selection medium also contains a compound for selection of transformed cells and is dependent on the selectable marker gene that is included in the *Agrobacterium*. Examples of compounds that can be used include plant active antibiotics or herbicides. The selection medium also preferably contains a compound that suppresses the growth of Agrobacterial cells. Such compounds are well known in the art and include cefotaxime, carbenicillin, and timentin. In one embodiment, the selection is performed in a small growth vessel, such as a multi-well plate. In one embodiment, the cells are cultured in a condition with 2000-3000 lux lighting with 16/8 hours day/night cycles, 26° C. 30° C. temperature and gentle shaking at 50-100 rpm. Somatic embryos thus produced are matured and germinated as those from solid medium. A desiccation step after the liquid stage may facilitate embryos germination. Alternatively, chemical agents, such as abscisic acid (ABA), that mimic the desiccation effect may be used.

The germinated transgenic plants are then transferred to soil to develop into flowering plants. The transgenic plants can be used as a parent in conventional breeding programs.

In another aspect, the present invention relates to a novel *Agrobacterium* strain which improves transformation efficiency. In one embodiment, the novel *Agrobacterium* strain contains a constitutively active virA gene. The strain needs no added chemicals for virulence induction. The virA gene is integrated into the chromosomal genome or Ti plasmid for improved stability. The novel *Agrobacterium* strain does not contain a wild type allele of virA. The virA gene is expressed in a super-virulent background, such as in a pTiBo542 background, and is derived from pTiBo542. In one embodiment, the novel *Agrobacterium* strain is AGL2. A culture of *Agrobacterium* strain AGL2 has been deposited under the Budapest Treaty on 28 Oct. 2009 with the American Type Culture Collection (ATCC), 10801 University Boulevard, Manassas, Va., 20110-2209 USA under ATCC® Patent Deposit Designation PTA-10447. The deposit has been tested for viability on 4 Nov. 2009 by the ATCC and the culture was viable.

In another aspect, the present invention relates to a novel *Agrobacterium* strain which improves regeneration efficiency. In one embodiment, the improved regeneration efficiency occurs at post-co-culture steps. In one embodiment, the novel *Agrobacterium* strain contains a mutation that leads to auxotrophy for growth. The novel *Agrobacterium* strain may further contain a mutant gene encoding a constitutively active virA protein. The virA protein is expressed in a super-virulent background, such as in a pTiBo542 background. In one embodiment, the novel *Agrobacterium* strain is AGL3. A culture of *Agrobacterium* strain AGL3 has been deposited under the Budapest Treaty on 28 Oct. 2009 with the American Type Culture Collection (ATCC), 10801 University Boulevard, Manassas, Va., 20110-2209 USA under ATCC® Patent Deposit Designation PTA-10448. The deposit has been tested for viability on 4 Nov. 2009 by the ATCC and the culture was viable.

In another aspect, the present invention provides a method for improved plant transformation efficiency. In this method, the embryogenic calli are co-cultured with an *Agrobacterium* strain in a medium that contains an inhibitor of NADPH oxidase. In one embodiment, the inhibitor of NADPH oxidase is diphenylene iodonium (DPI) in the range between about 1 µM and about 50 µM, preferably between about 1 µM and about 10 µM.

Techniques for co-culture of embryogenic calli with an *Agrobacterium* are well known in the art. Any strain harboring a DNA construct that contains a gene or nucleic acid of interest can be used. A preferred method for co-culture is the method that is disclosed in International Publication No. WO 2005/103271.

The polynucleotide that is inserted (the polynucleotide of interest) into plants in accordance with the present invention is not critical to the transformation process. Generally the polynucleotide of interest that is introduced into a plant is part of a construct. The polynucleotide of interest may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (International Publication No. WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142. Jatropha promoters include those disclosed in U.S. provisional patent application No. 61/184,416.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880. Tissue preferred Jatropha promoters include those disclosed in U.S. provisional patent application No. 61/184,416.

Where appropriate, the polynucleotide of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, Molecular biology of plants: a laboratory course manual (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press. New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Barnes & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1.984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference* (RNAi): *The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Media Formulations

J20P: $NH_4NO_3$-free MS salts, MS vitamins, 20 g/l sucrose, 50 g/l PEG 8000, 0.5 g/l glutamine, 0.25 g/l asparagine, 0.2 mg/l 2,4-D sodium salt, pH 5.8

IM (Chilton et al., 1974; de Groot et al., 1998): 2.05 g/l $K_2HPO_4$, 1.45 g/l $KH_2PO_4$, 0.6 g/l $MgSO_4$-$7H_2O$, 0.5 g/l $(NH_4)_2SO_4$, 0.5 g/l $NH_4NO_3$, 0.01 g/l $CaCl_2$, 0.5 mg/l $ZnSO_4$-$7H_2O$, 0.5 mg/l $CuSO_4$-$5H_2O$, 0.5 mg/l $H_3BO_3$, 0.5 mg/l $MnSO_4$—$H_2O$, 0.5 mg/l $NaMbO_4$-$2H_2O$, 1 mg/l $FeSO_4$, 0.5% glycerol, 0.5 g/l 2-[N-morpholino]ethanesulfonic acid (MES), 0-100 µM acetosyringone, 2 g/l glucose, pH 5.7-5.8

JIM2: IM medium plus: B5 vitamins, 2 mg/l 2,4-D, 1-50 diphenylene iodonium (DPI).

JIM2 solid: JIM2 with 2 g/l phytagel.

JIM2H: JIM2 medium plus 0.3 g/l histidine.

JIM2H solid (for co-culture): JIM2H with 2 g/l phytagel.

Bd2: Gamborg B5 salts, B5 vitamins, 30 g/l sucrose, 2.2 g/l phytagel, 2 mg/l 2,4-D sodium salt, pH5.8.

DGA: $NH_4NO_3$-free MS salt, Gamborg B5 vitamins, 30 WI sucrose, 2.4 g/l phytagel, 1 g/l glutamine, 0.5 g/l asparagine, pH 5.8.

M9-2: $NH_4NO_3$-free MS salts, Gamborg B5 vitamins, 20 g/l sucrose. 20 g/l maltose, 1 g/l glutamine, 0.5 g/l asparagine, 2.4 g/l phytagel, 0.1 g/l casein hydrolysate, pH 5.8.

G35-2: MS salts, vitamins, 20 g/l sucrose, 5 g/l agar, 0.1 g/l casein hydrolysate, 2 mg/l gibberellic acid ($GA_3$), pH 5.8.

W9: MS salts, MS vitamins, 20 g/l sucrose, 1 mg/l $FeSO_4$, 0.1 g/l casein hydrolysate, 0.01 mg/l α-naphthaleneacetic acid (NAA), 5.5 g/l agar, pH 5.8.

W15: ½ MS salts, ½ MS vitamins, 15 g/l sucrose, 1 mg/l $FeSO_4$, 0.1 activated charcoal, 0.1 g/l casein hydrolysate, 0.01 mg/l NAA, 5 g/l agar, pH 5.8.

Example 2

Co-Culture of Embryogenic Calli with *Agrobacterium*

Embryogenic cell lines, for example, JS4 cell line, which was derived from a zygotic embryo of an Indonesian *Jatropha curcas* collection, were subcultured every week by transferring about 3 g of the cell mass to 20 ml J20P medium. 3-5 days after subculture, the embryogenic calli cell mass was collected.

Co-culture plates were made by pouring about 30 ml JIM2H solid medium to each 90 mm Petri dish. Alternatively, 3-4 sheets of cellulose filter paper can be soaked with JIM2H liquid medium before placing into a 90 mm Petri dish. One sheet of 82 mm Hybond N membrane was over-laid to the medium-soaked cellulose filter paper or solid JIM2H medium. About 0.75 g embryogenic calli was mixed with 200 ul *Agrobacterium* cells on the membrane. After one hour incubation at room temperature, excess liquid medium containing the *Agrobacterium* cells was removed. The plates were capped, sealed with 3M tape and incubated at 24° C. with dim light for 2-3 days.

Example 3

Preparation of *Agrobacterium* Cultures

Fresh colonies of AGL2 or AGL3 harboring pCambia1305.1 were inoculated into 30 ml LB medium that had been supplemented with 25 mg/l rifampicin and 50 mg/l kanamycin. Cells were cultured at 28° C., 200-230 RPM until OD600 reached 0.8-2.0. The culture was diluted to 0.3 OD600 units with LB medium with appropriate antibiotics and incubated in the same condition for about 2-3 hr at 28° C. until about 0.6 OD600 unit. 25 ml of the *Agrobacterium* culture were transferred to a 50 ml Falcon tube and the cells were spun down at 3500 RCF, 15° C. for 20 min in a benchtop centrifuge with a swing-out rotor. The LB medium was removed and the pellet was resuspended in 25 ml JIM2H medium. The cells were allowed to induced at room temperature with no shaking for about 2 hours and the *Agrobacterium* preparation was adjusted to about 0.5 OD600 using the same medium.

For transformants of wt AGL1 strain, the cells were cultured in the *Agrobacterium* MinAB medium and pre-induced in induction medium (IM) supplemented with AS for about 6 hours before being used for co-culture with plants cells.

Example 4

Selection and Regeneration of Transformants

The co-cultured somatic embryogenic calli were washed for three times on the membrane with Bd2 medium supplemented with 5-1.0 mg/l hygromycin and 300 mg/l cefotaxime. The calli were transferred to solid Bd2 medium supplemented with 5-10 mg/l hygromycin and 300 mg/l cefotaxime. The plates were placed in a 26° C. tissue culture room with 16 hr lighting per day on shelves with one 36 W Phillips Lifemax light tube (warm light). Subculture was done in the same fresh medium after 2-3 weeks. In another 4-6 weeks, resistant calli were transferred to DGA medium supplemented with 7 mg/l hygromycin and 300 mg/L cefotaxime. In about 3-4 weeks, small green cotyledonary stage embryo appeared. They were transferred to M9-2 medium supplemented with 7 mg/l hygromycin and 300 mg/l cefotaxime.

In about 3 weeks, the embryos were transferred to G35-2 medium with 10 mg/l hygromycin. At this stage, up to four 36 W light tubes may be used. Lighting remains 16 hr per day. In about 3-4 weeks, germinated embryos were transferred to W9 medium with 7 mg/l hygromycin. In about 2-3 weeks, the plantlets were transferred to W15 medium (without hygromycin). Rooted plantlets were ready for planting in soil in 2-3 weeks.

Selection for transformants can also be done with herbicides, such as glyfosinate, and other antibiotics, such as kanamycin.

Selection on solid medium was always associated with heavy *Agrobacterium* over-growth, which kills the majority of transgenic calli/somatic embryos. Table 1 summarizes the numerous examples of selection using this approach.

TABLE 1

Selection of Transgenic Jatropha Plants on Various Media

| Code | Date | Strain | Plasmid | Calli Source | Selection Method | Results |
|---|---|---|---|---|---|---|
| TE1 | Oct. 6, 2007-Oct. 30, 2008 | AGL1 | pST2eGFP | solid medium SE | SE on solid medium | no transformants due to heavy Agro contamination |
| TE2 | Oct. 30, 2007-Oct. 30, 2008 | AGL1 | pST2eGFP | liquid medium SE | SE on solid medium | no transformants due to heavy Agro contamination |
| TE3 | Nov. 5, 2007-Oct. 30, 2008 | AGL1 | pST2eGFP | liquid medium SE | SE on solid medium | no transformants due to heavy Agro contamination |
| TE4 | Nov. 20, 2007-Mar. 6, 2008 | AGL1 | pST2eGFP | liquid medium SE | SE on solid medium with Kan-LMP coating | no transformants due to heavy Agro contamination |
| TE5 | Nov. 27, 2007-Mar. 6, 2008 | AGL1 | pPZP11135SGFP | liquid medium SE | SE on Kan solid medium with Kan-LMP coating | no transformants due to heavy Agro contamination |

TABLE 1-continued

Selection of Transgenic Jatropha Plants on Various Media

| Code | Date | Strain | Plasmid | Calli Source | Selection Method | Results |
|---|---|---|---|---|---|---|
| TE6 | Jan. 8, 2008-Feb. 12, 2008 | AGL1 | pC1305.1 | liquid medium SE | Hyg 0, 10, 20, 30 and 50 mg/l SE on solid medium | no transformants due to heavy Agro contamination high selection pressure |
| TE7 | Jan. 14, 2008-Feb. 19, 2008 | AGL1 | pST2eGFP | liquid medium SE | Kan 0, 25, 50 and 80 mg/l SE on solid medium | 50-80 mg/l OK, heavy Agro contamination DPI caused no damage on explants |
| TE8 | Jan. 15, 2008-Feb. 18, 2008 | AGL1 | pC1305.1 | liquid medium SE | Hyg 0, 10, 20, 30 and 50 mg/l SE on solid medium | Agro contamination, NA did not kill agrobacterial cells too high selection pressure |
| TE10 | Jan. 30, 2008-Mar. 4, 2008 | AGL1 | pC1305.1 | liquid medium SE | Hyg 0, 10, 20, 30 and 50 mg/l SE on solid medium | NA able to inhibit AGL1 at 80 mg/l yet ineffective no effect on plant cells |
| TE11 | Feb. 3, 2008-Mar. 4, 2008 | AGL1 | pCI305.1 | liquid medium SE | Hyg 0, 2, 4, 5, 6 and 8 mg/l SE on solid medium | no transformants due to heavy Agro contamination |
| TE14 | Mar. 3, 2008-Oct. 30, 2008 | AGL1 | pC1305.1 bar | liquid medium SE | GLF 0, 2, 5 and 10 mg/l SE on solid medium | no transformants due to heavy Agro contamination |
| TE19 | Mar. 23, 2008-Dec. 23, 2008 | LBA4404 | pC1305.1 bar | liquid medium SE | GLF 0, 5, 8 and 10 mg/l SE on solid medium | no transformants due to heavy Agro contamination |
| TE26 | May 9, 2008-Jan. 23, 2009 | LBA4404 | pC1305.1 bar | liquid medium SE | GLF 3 and 5 mg/l SE on solid medium | no transformants due to heavy Agro contamination |
| TE29 | Jun. 23, 2008-Jan. 23, 2009 | LBA4404 | pC1305.1 bar | liquid medium SE | GLF 3, 5 and 8 mg/l MSO 1 µM SE on solid medium | no transformants due to heavy Agro contamination |
| TE32 | Jul. 21, 2008-Jan. 23, 2009 Mar. 18, 2009 | LBA4404 9, 12 cm | pC1305.1 bar | liquid medium SE and SEC | GLF 10 and 5 then 10 mg/l SEC/SE on solid medium | no transformants due to heavy Agro contamination |
| TE34 | Jul. 25, 2008-Jan. 23, 2009 | LBA4404 | pC1305.1 bar | liquid medium SEC | GLF 5, 10 mg/l SEC embedded in LMP medium | no transformants due to heavy Agro contamination |
| TE37 | Aug. 1, 2008-Jun. 17, 2009 | AGL2 | pC1305.1 | liquid medium SEC | Hyg 0, 1, 2, 5, mg/l SEC embedded in LMP medium | transgenic plant generated Southern blot positive, potted to soil |
| TE40 | Aug. 8, 2008-Jun. 3, 2009 | AGL2 | pC1305.1 bar | liquid medium SEC | GLF 3 and 5 mg/l SEC embedded in LMP medium | after intense rescue effort from contamination, one resistant plant obtained. GUS staining positive |
| TE43 | Aug. 15, 2008-Jun. 3, 2009 | AGL1 AGL2 | pC1305.1 bar | liquid medium SEC | GLF 0, 3, 5 and 10 mg/l SEC embedded in LMP medium | 1 resistant plant by AGL1. number too small to draw conclusion. GUS staining positive |
| TE45 | Aug. 19, 2008-May 21, 2009 | AGL1 AGL2 | pC1305.1 bar | liquid medium SEC | GLF 0, 3, 5 and 10 mg/l SEC embedded in LMP medium | 1 resistant plant by AGL1. number too small to draw conclusion. GUS staining positive |
| TE46 | Aug. 19, 2008-Apr. 18, 2009 | LBA4404 | pC1305.1 bar | liquid medium SEC | GLF 0, 3, 5 and 10 mg/l SEC embedded in LMP medium | no resistant plant |

TABLE 1-continued

Selection of Transgenic Jatropha Plants on Various Media

| Code | Date | Strain | Plasmid | Calli Source | Selection Method | Results |
|---|---|---|---|---|---|---|
| TE48 | Aug. 26, 2008-Apr. 9, 2009 | AGL2 | pC1305.1 bar | liquid medium SEC | GLF 0, 5 and 10 mg/l SEC embedded in LMP medium | no resistant plant |
| TE49 | Aug. 25, 2008-May 6, 2009 | AGL2 | pC1305.1 bar | liquid medium SEC | GLF 0, 5 and 10 mg/l SEC embedded in LMP medium | 1 resistant plant, potted |
| TE50 | Sep. 7, 2008-Apr. 9, 2009 | LBA4404 | pC1305.1 bar | liquid medium SEC | GLF 0 and 5 mg/l SEC embedded in LMP medium | no resistant plant |
| TE51 | Sep. 9, 2008-Apr. 9, 2009 | AGL2 | pC1305.1 bar | liquid medium SEC | GLF 0 and 10 mg/l SEC embedded in LMP medium | no resistant plant heavy contamination |
| TE52 | Sep. 12, 2008- | AGL1 AGL2 | pC1305.1 bar | liquid medium SEC | GLF 0, 5 and 10 mg/l SEC embedded in LMP medium | no resistant plant heavy contamination |
| TE53 | Sep. 19, 2008-Jun. 30, 2009 | AGL2 | pC1305.1 | liquid medium SEC | Hyg 0, 5, 6, 8 and 10 mg/l SEC embedded in LMP medium | got resistant plants. GUS staining positive optimal Hyg 6-8 mg/l |
| TE54 | Oct. 3, 2008-Feb. 12, 2009 | AGL2 | pC1305.1 bar | liquid medium SEC | GLF 0, 5, 10, 20, 30 and 50 mg/l SEC embedded in LMP medium | no resistant plant |
| TE55 | Oct. 9, 2008-Jan. 30, 2009 | AGL2 | pC1305.1 | liquid medium SEC | Hyg 0, 8 mg/l SEC embedded in LMP medium | heavy agro contarmination |
| TE56 | Nov. 4, 2008-Jul. 18, 2009 | AGL2 | pC1305.1 | liquid medium SEC | Hyg 0, 2, 3, 5 mg/l then 7 mg/l SEC embedded in LMP medium | transgenic plant generated, Southern positive, potted to soil |
| TE57 | Nov. 21, 2008-Feb. 3, 2009 | AGL2 | pC1305.1 bar | liquid medium SEC | MSO 0, 1, 2, 5, 10 and 20 μM SEC embedded in LMP medium | no resistant plant |
| TE58 | Nov. 21, 2008-Mar. 3, 2009 | AGL2 | pC1305.1 bar | liquid medium SEC | GLF 5 mg/l then 30 mg/l SEC embedded in LMP medium | no resistant plant |
| TE59 | Dec. 2, 2008- | AGL2 | pC1305.1 | liquid medium SEC | Hyg 0 and 7 mg/l SEC embedded in LMP medium | cell line 1: 9 trasngenic lines from 5 co-culture cell line 2: none from 2 co-culture cell line 3: 1 transgenic line from 2 co-culture cell line 4: none from 3 co-culture |
| TE60 | Dec. 5, 2008- | AGL2 | pC1305.1 | liquid medium SEC | Hyg 0 and 8 mg/l SEC embedded in LMP medium | cell line 1, 5 transgenic lines from 3 co-culture cell line 2: 1 transgenic line from 3 co-culture cell line 3: 3 transgenic lines from 3 co-culture cell line 4: 2 transgenic lines from 2 co-culture |

TABLE 1-continued

Selection of Transgenic Jatropha Plants on Various Media

| Code | Date | Strain | Plasmid | Calli Source | Selection Method | Results |
|------|------|--------|---------|--------------|------------------|---------|
| TE61 | Jan. 8, 2009- | AGL2 | pC1305.1 | liquid medium SEC | Hyg 0, 2, 5, 1 and 10 mg/l then shifted to 7 mg/l SEC embedded in LMP medium | 90 hyg resisisiant plants, 48 GUS positive plants from 6 co-culture 30% GUS negative plants contained transgene 46% dish discarded due to agrobacterium overgrowth |

Notes:
IM with AS: Agrobacterium induction medium with 200 μM acetosyringone.
Kan: kanamycin.
Hyg: hygromycin.
GLF: glyfosinate.
SE: somatic embryos.
SEC somatic embryogenic calli.
MSO: methionine sulfoximine Alternatively, co-cultured somatic embryogenic calli were washed for three times on the membrane with Bd2 medium supplemented with 5-10 mg/l hygromycin and 300 mg/l cefotaxime. About 0.1 g co-cultured calli was spread at low density on solid Bd2 medium supplemented with 5-10 mg/l hygromycin and 300 mg/l cefotaxime. Ten ml low melting point (LMP) agarose (0.6%) containing Bd2 medium supplemented with 5-10 mg/l hygromycin and 300 mg/l cefotaxime was over-laid to a Bd2 solid medium plate that contains the same selection agents. The plates were placed in a 26° C. tissue culture room with 16 hr lighting per day on shelves with one 36 W Phillips Lifemax light tube (warm light). Calli embedded in LMP agarose medium at low density reduced plate contamination rate from >90% to about 50% (TE 61).

Selection in the LMP medium was done for 8-10 weeks until cotyledonary stage embryos were produced. Subculture was done by carefully picking up resistant calli, placing on a fresh Bd2 medium and overlayed with LMP Bd2 medium. Resistant embryos at torpedo to cotylendonary stages were transferred to DGA medium supplemented with 7 mg/l hygromycin and 300 mg/L cefotaxime. In about 3-4 weeks, small green cotyledonary stage embryo appeared. They were transferred to M9-2 medium supplemented with 10 mg/l hygromycin and 300 mg/l cefotaxime. In about 3 weeks, the embryos were transferred to G35-2 medium with 10 mg/l hygromycin. At this stage, up to four 36 W light tubes may be used. Lighting remains 16 hr per day. In about 3 weeks, germinated embryos were transferred to W9 medium with 10 mg/l hygromycin. In about 2-3 weeks, the plantlets were transferred to W15 medium (without hygromycin). Rooted plantlets were ready for planting in soil in 2-3 weeks.

Numerous hygromycin resistant somatic embryos were observed with embryogenic calli co-cultured with *Agrobacterium* strains harboring pCambia1305.1 when selection was done by the medium embedding method (FIG. 1).

Example 5

Construction of *Agrobacterium tumefaciens* Mutants AGL2 and AGL3

AGL1-ΔvirA strain: An approximately 10-kb fragment that contains the AGL1 virA gene in pUC18-SfiI was isolated from a genomic library of AGL1 using C58 virA gene as a probe. A 4.6-kb fragment containing entire AGL1 virA gene was made by digestion with AscI and KpnI and subcloned into pUC18-SfiI to generate pUC18-virA. A 1.4-kb hygromycin cassette with flanking with loxP sites was cloned into the pUC18-virA that was cut with NheI and BglII to produce pUC18-ΔvirA-Hyg, from which the entire ΔvirA cassette was released by digestion with SfiI and inserted into pUT-mini-Tn5-sp, creating pTn5-ΔvirA-Hyg.

Two plasmids pPZP200-virB::LacZ (spectinomycin resistance) and pRil5A-Tac::RecA (kanamycin resistance, containing the RecA gene from *A. tumefaciens* C58) were co-introduced into supervirulent *A. tumefaciens* strain AGL1 (pTiBo542 in C58 chromosomal background) (Lazo et al., 1991) by electroporation, the transferred strain was named AGL1(LacZ RecA). The virB::LacZ fusion gene was used as a reporter gene for monitoring the functionality of virA gene of AGL1 while the RecA gene restores the recombintion function AGL1 so that knockout of virA could be achieved. The suicide vector pTn5-ΔvirA-Hyg was delivered from the donor strain *E. coli* S17-1 (λpir) to the recipient strain AGL1 (LacZ RecA) by hi-parental mating at 28° C. Conjugants were selected on MiniAB agar containing hygromycin (100 μg/ml) and rifampicin (50 μg/ml) as well as 5-bromo-4-chloro-3-indolyl-galactoside (X-Gal; 40 μg/l). Nine randomly selected colorless colonies were transferred to liquid MiniAB or 2YT with the same antibiotics. The Southern analysis confirmed deletion of the virA (not shown).

The two plasmids in AGL1-ΔvirA were removed by growing the cells in liquid MiniAB without antibiotics at 36° C. consecutively for 6 days with 3 subcultures in between. After streaking on 2YT medium, 84 colonies were tested for growth in medium with spectinomycin (50 ug/ml), kanamycin (25 μg/ml) or hygromycin (100 μg/ml) respectively. Only one colony (named 8D12) was found to have lost both spectinomycin and kanamycin resistance, but it has maintained hygromycin resistance.

To remove hygromycin resistance from strain 8D12, plasmid pRil5A-Tac::Cre which contains the site-specific DNA recombinase gene Cre was introduced into the strain 8D12 by electroporation. The transformants were incubated in 2YT supplemented with kanamycin (25 μg/ml) and rifampicin (50 μg/ml) at 28° C. for 2 days. Colonies that had lost resistance to hygromycin were selected. Plasmid pRil5A-Tac::Cre was cured according to the above mentioned method. One such colony, ΔA4-4, which was sensitive to spectinomycin, kanamycin and hygromycin was selected as the AGL1-ΔvirA strain.

AGL2 strain: virA protein containing mutation G665D has been shown to strongly activate vir gene expression in the absence of acetosyringone and monosaccharides (McLean et al., 1994). The work was done in non-supervirulent octopine strain and the functionality and efficacy of virA at the corresponding site was unknown.

To re-introduce mutated virA gene into AGL1-ΔvirA, a ~3.5-kb fragment containing the entire VirA gene promoter, coding sequence containing G665D mutation and 3' flanking sequence (including virJ promoter) was created by fusion of two PCR fragments over-lapping at the G665D residue, which as made by primer-directed mutagenesis. The fused PCR product was cloned into plasmid pUC18-SfiI to product pUC18-virA-on. Subsequently, a 1.4-kb hygromycin cassette with flanking loxP sites was inserted into downstream of VirA-on gene to generate pUC18-virA-on-Hyg. Meanwhile, plasmid pRil5A-Tac::RecA was re-introduced into *A. tumefaciens* strain ΔA4-4 by electroporation to make strain ΔA4-4R. pUC18-virA-on-Hyg was introduced to ΔA4-4R and transformants containing the constitutive virA mutant were selected on MiniAB agar supplemented with hygromycin (100 μg/ml) and rifampicin (50 μgml). One hygromycin and rifampicin-resistant colony was picked and presence of the constitutive virA gene was confirmed by X-gal staining after introducing pPZP200-virB::LacZ.

After curing of pRil5A-Tac::RecA, pRil5A-Tac::Cre was introduced back into the strain so as to excise the hygromycin resistance gene cassette. After curing of the hygromycin sensitive strains, AGL2 strain was created. Molecular analysis showed that the virA-on gene was integrated at the loxP site next to the deleted virA.

To confirm that the AGL2 retains the full supervirlence and independence of AS for vir gene induction, pPZP200-virB::LacZ was introduced into the strain and its lacZ activity in AS-free media was compared to that of wt AGL1 induced with 100 μM AS. Results showed that AGL2 expressed comparable LacZ protein in AS-free IM media to that of wt AGL1 with 100 μM AS. (not shown).

Several versions of virA mutants were made in AGL1 background, eg., C58 virA G665D mutant and AGL1 virA G665D mutant linked to the strong *E. coli* tac promoter or AGL1 virG promoter. All were several folds weaker than AGL2.

To further confirm that AGL2 was able to deliver T-DNA into host cell, pEX2 was tested for transformation efficiency by this strain in *Ustilago maydis*. Surprisingly, AGL2 outperformed AGL1 in producing transgenic cells (Table 2). Similar enhancing effect was seen in transformation of *U. scitaminae* and *Aspergillus niger*. Southern blot analyses showed no significant differences from the wild type AGL1 with regard to T-DNA transfer fidelity and copy number.

TABLE 2

Transformation of *Ustilago maydis* Without vir Inducer

|  | CFU/plate | Average CFU/plate |
|---|---|---|
| AGL1 + AS | 110/115/211 | 145 |
| AGL2 + AS (colony No. 1) | 80/105/91 | 92 |
| AGL2 + AS (colony No. 2) | 107/120/115 | 114 |
| AGL2 No AS (colony No. 1) | 840/590/660 | 696 |
| AGL2 No AS (colony No. 2) | 590/580/667 | 612 |

Note:
Agrobacterium cells transformed with pEX2 (100 μl, OD600 = 0.3) were cultured in IM medium (de Groot et al., 1998) for 6 hour before co-cultured with *U. maydis* sporidia (100 μl, OD600 = 0.7) for 48 hr. Selection for transformants was done by placing the membranes on YPD medium with 150 μm/ml hygromycin B and 300 μg/ml cefotaxime.

AGL2 was further tested for AS-independence in plant transformation. Cotton somatic embryogenic calli were co-cultured with AGL2(pST2-EGFP) or AGL1(pST2-EGFP) in the presence or absence of 100 μM AS. Selection for transformants was done by transferring the calli clumps to solid medium as described in PCT application WO/2005/103271. About 60-70% calli gave rise to kanamycin resistant somatic embryos when AGL2(pST2-EGFP) was used for co-culture with no AS added. This is essentially the same as that achieved with AGL1 that was supplemented with 100 μM AS.

Auxotrophic strains of AGL2: Transposon plasmid pTn5-Hyg was constructed by replacing spectinomycin resistance gene in pUC-miniTn5-sp-eGFP with a 1.4-kb hygromycin cassette flanked with loxP sites. pRil5A-Tac::RecA was introduced into AGL2 and transposon Tn5-Hyg was transferred from *E. coli* S17-1 (λpir) to the *Agrobacterium* strain by bi-parental conjugation at 28° C. Conjugants were selected on 2YT agar containing hygromycin (100 μg/ml) and chloramphenicol (20 μg/ml). Resistant colonies were transferred in duplicates to both 2YT medium and MS medium. Colonies that failed to grow in MS medium were inoculated in 2 ml 3YT medium with hygromycin and chloramphenicol. The overnight cultures were pelleted, washed with MS medium and re-inoculated in MS medium supplemented with various amino acids, such as arginine (R), asparagine (N), glutamic acid (E), glutamine (Q), histidine (H), leucine (L), lysine (K) and proline (P). From 5000 transposon conjugants, 5 auxotrophic strains were isolated. Among them strain No. 14 and No. 22 required histidine for growth in MS medium. Strain 14 was cured of pRil5A-Tac::RecA and the hygromycin resistance cassette was removed by the Cre recombinase as described previously and the hygromycin sensitive derivative was named AGL3.

Example 6

Figure 2:
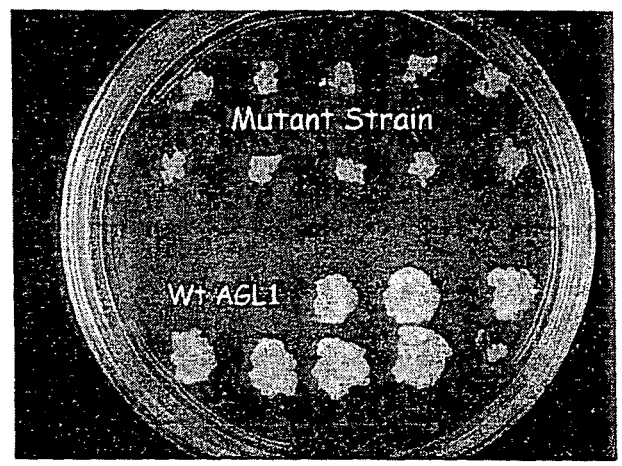
FIG. 2 shows embryogenic calli that were co-cultured with either AGL2(pCambia1305.1) or AGL3(pCambia1305.1). 0.3 mg/l histidine was added in all media before or during the co-culture stage. Thoroughly washed calli were transferred in small clumps on solid Bd2 medium supplemented with 7 mg/l hygromycin and 300 mg/l cefotaxime and cultured under the same condition. The plate was photographed 4 weeks after the first culture on solid selection medium.

Effective Control of *Agrobacterium* Over-Growth During Selection Stage by the Use of Auxotropic *Agrobacterium* Strains Embryogenic calli were co-cultured with either AGL2 (pCambia1305.1) or AGL3(pCambia1305.1) as described in Example 2. 0.3 mg/l histidine was added in all media before or during co-culture stage. Thoroughly washed calli were transferred in small clumps on solid Bd2 medium supplemented with 7 mg/l hygromycin and 300 mg/l cefotaxime and cultured under the same condition for 4 weeks. Only 1 in 8 calli sector was free of *Agrobacterium* cells while the rest was covered with thick layer of *Agrobacterium* cells. In contract, all 10 calli sectors co-cultured with AGL3 showed no sign of *Agrobacterium* contamination and the calli showed healthy growth (greenish color) under the selection medium, indicating generation of transformed somatic embryos (FIG. 2).

Example 7

Improved Transformation Efficiency of Constitutive virA Strain

Figure 3:
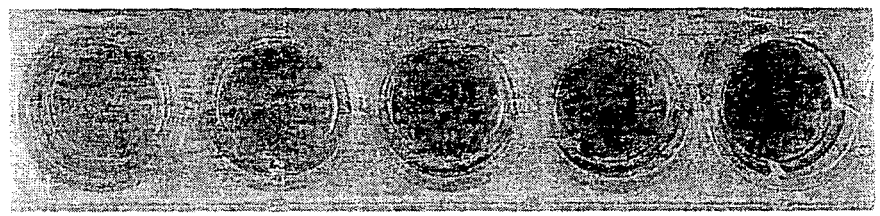
FIG. 3 shows embryogenic calli that were co-cultured for 53 hours with either AGL1(pCambia1305.1 bar) or AGL2 (pCambia1305.1 bar) in medium with (200 μM) or without AS as described in Example 2. The calli were immediately stained with X-gluc and photographed.

Embryogenic calli were co-cultured for 53 hours with either AGL1(pCambia1305.1 bar) or AGL2(pCambia1305.1 bar) in medium with or without AS (200 μM) as described in Example 2. The calli were immediately stained with X-gluc. Stronger blue staining was observed in all calli co-cultured with AGL2 and AS further boosted transformation efficiency in AGL2 (FIG. 3).

Example 8

Improved Transformation Efficiency by the Use of DPI

Figure 4:
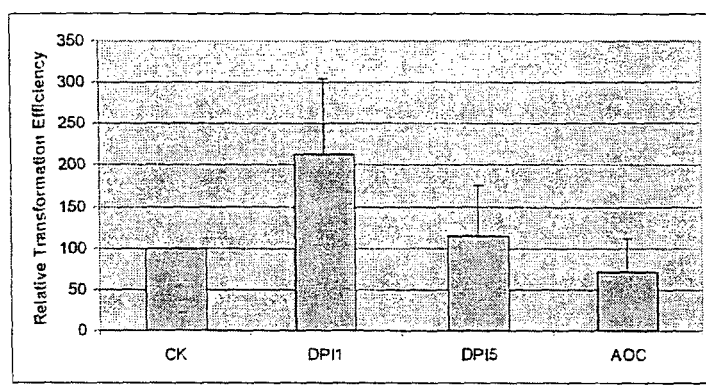
FIG. 4 shows somatic embryogenic calli from 4 different cell lines that were co-cultured with AGL2(pCambia1305.1) and selection was done by embedding the calli in LMP Bd2 medium. The co-culture medium JIM2 was supplemented with either 1 μM diphenyl iodonium (DPI), 5 μM DPI or a mixture of antioxidants with a final concentration of 1 mM Na-thiosulfate, 8.8 mM L-cysteine and 1 mM dithiothreitol (DTT). Hygromycin resistant somatic embryos were scored after two months selection. The number of somatic embryos derived from co-culture with DPI-free JIM2 (CK) was set at 100 in each cell line and the relative number of somatic embryos in other co-culture conditions was calculated by dividing the actual number by that of CK. The results derived from the average of four cell lines, each cell line consisting of 6 selection plates. "AOC" indicates culture medium with 1 mM Na-thiosulfate, 8.8 mM L-cysteine and 1 mM DTT.

Somatic embryogenic calli from 4 different cell lines were co-cultured with AGL2(pCambia1305.1) and selection was done by the LMP Bd2 embedding method. The co-culture medium JIM2 was supplemented with either 1 µM DPI, 5 µM DPI or a mixture of antioxidants with a final concentration of 1 mM Na-thiosulfate, 8.8 mM L-cysteine and 1 mM DTT. Hygromycin resistant somatic embryos were scored after two months selection. In transformation using each cell line, the number of somatic embryos derived from co-culture with DPI-free JIM2 (CK) was set at 100 and relative number of somatic embryos in other co-culture conditions was calculated by dividing the actual number by that of CK. The results (FIG. 4) clearly demonstrate that DPI at about 10 µM improved transformation efficiency by more than 2 folds whereas the combination of 1 mM Na-thiosulfate, 8.8 mM L-cysteine, 1 mM DTT led to little improvement.

The transformation enhancing effect of DPI was also tested in soybean. Soybean embryogenic suspension culture (derived Peking 18) was co-cultured for 2.5 day at 24° C. with pre-induced AGL1(pCambia1305.1) on nylon membrane, which was placed on top of solid medium (1M with 20 mg/l 2,4-D and B5 vitamins) that was supplemented with 1 µM DPI or 1 mM Na-thiosulfate, 8.8 mM L-cysteine and 1 mM DTT. After selection with 10 mg/l hygromycin, the calli clumps were stained with X-gluc. GUS staining was observed in about 40% calli clumps that was co-cultured the control medium (with 20 mg/l 2,4-D and B5 vitamins). In contrast, more than 80% calli clumps showed GUS staining when 1 µM DPI was added in the co-culture medium. Surprisingly, combination of 1 mM Na-thiosulfate, 8.8 mM L-cysteine and 1 mM DTT did not improve transformation rate in our co-culture system.

Example 9

Analyses of Transgenic Plants

Figure 5:
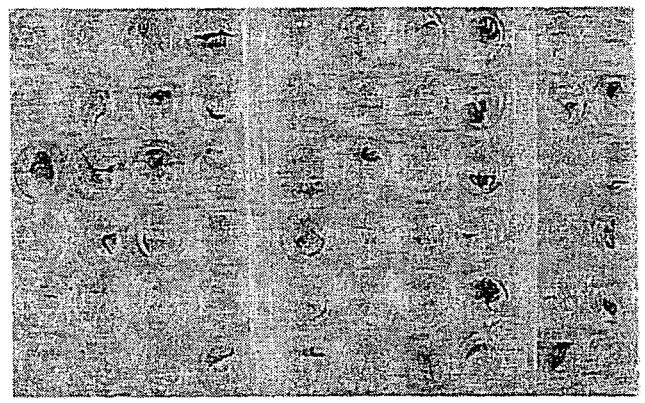
FIG. 5 shows somatic embryos vigorously developing in selection medium that were selected about 2 months after co-culture and small pieces of the leaf tissues were removed and placed in a well in a microtitre plate filled with 200 μl phosphate buffer (50 mM) with 1 mM X-gluc. After vacuum infiltration, the tissue was incubated at 37° C. overnight and the tissue was cleared with 70% ethanol.

Somatic embryos vigorously developing in selection medium were selected about 2 months after co-culture and small pieces of the leaf tissues were removed and placed in a well in a microtitre plate filled with 200 µl phosphate buffer (50 mM) with 1 mM X-gluc (5-bromo-4-chloro-3-indolyl beta-D-glucuronide). After vacuum infiltration, the tissue was incubated at 37° C. overnight and the tissue was cleared with 70% ethanol. Usually, 50-60% somatic embryos were positive for the staining (FIG. 5). More than 140 hygromycin resistant plants were produced from co-culture of about 1.5 g embryogenic calli.

Figure 6:
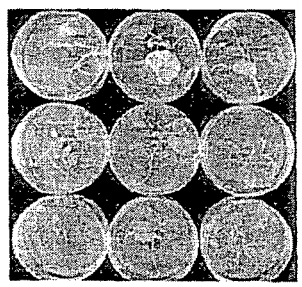
FIGS. 6A-6C show hygromycin resistant plantlets 4 months after co-culture.
Figure 6:
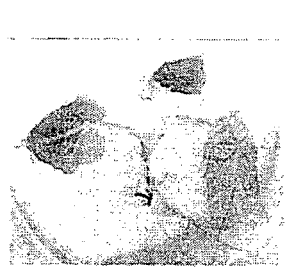
Figure 6:
Figure 7:
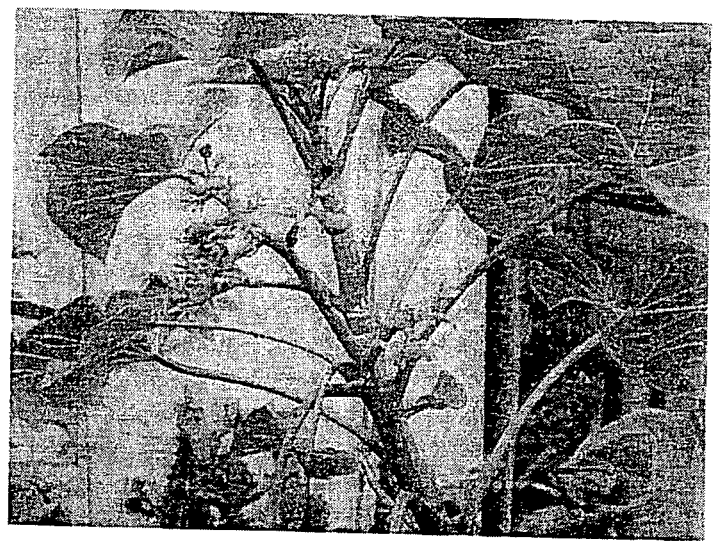
FIG. 7 shows an example of flowering transgenic plant with developing fruits.

About 4 months after co-culture, fully developed plantlet were ready for transplantation in soil (FIG. 6A). Chimera was not observed in 10 plantlets stained. (FIG. 6B). The plants show no sign of developmental abnormality (FIG. 6C) and normal flowers and fruits were produced (FIG. 7). As expected, T1 seeds segregate into GUS positive and GUS negative off-springs with no sign of chimera for the transgene.

Figure 8:
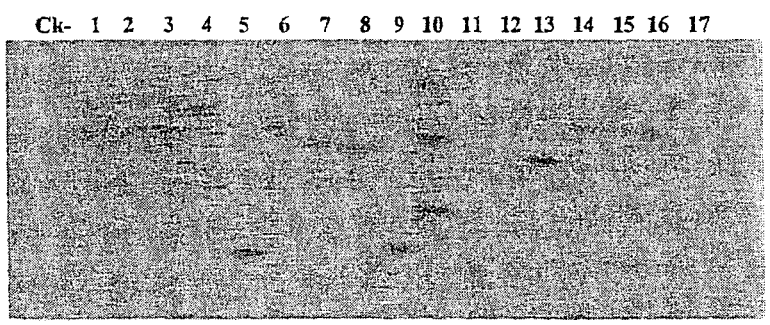
FIG. 8 shows Southern blot analysis of 17 randomly selected transgenic plants. Ck lane is DNA of wild type *Jatropha curcas* plant.

Total DNA was extracted from the hygromycin resistant plants and Southern blot was performed using the hpt gene as a probe. Only 1 in 17 plants did not contain the transgene (FIG. 8).

Example 10

Selection in Liquid Medium

Figure 9:
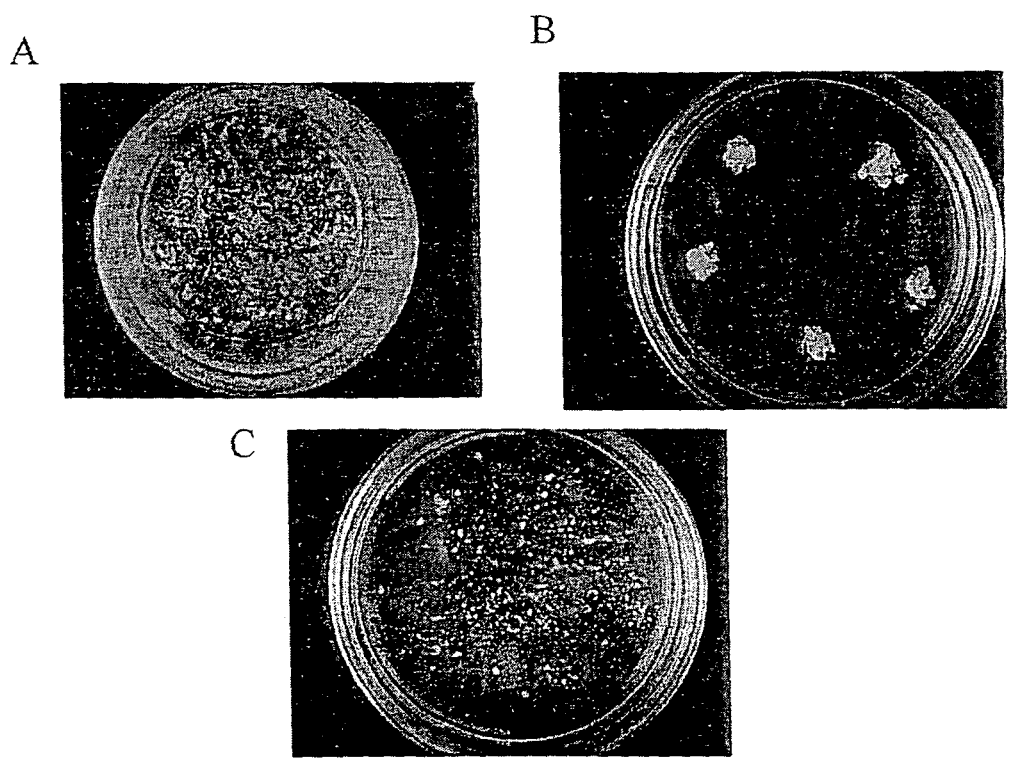
FIGS. 9A-9C show *Jatropha curcas* somatic embryogenic calli.

*Jatropha curcas* somatic embryogenic calli were co-cultured with AGL3(pCambia1305.1) for 2.5 days and selection was done in J20P medium with 7 mg/l hygromycin and 300 mg/l cefotaxime for three weeks. Subculture was done in a similar medium with reduced sucrose (10 g/l) for another 2 weeks. Resistant cotyledonary stage somatic embryos starting to emerge along with earlier stage embryos (FIG. 9A). This was about 3-4 weeks faster than those from selection on solid Bd2 medium (FIG. 9B) or embedded in LMP Bd2 (FIG. 9C).

The use of the terms "a" and "an" and "the" and similar referents in the context of describing the invention (especially in the context of the following claims) are to be construed to cover both the singular and the plural, unless otherwise indicated herein or clearly contradicted by context The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

BIBLIOGRAPHY

Bundock, P. et al. (1995). Trans-kingdom T-DNA transfer from *Agrobacterium tumefaciens* to *Saccharomyces cerevisiae*. *Embo J* 14:3206-3214.

Cerdeira, A. L. and Duke, S. O. (2006). The current status and environmental impacts of glyphosate-resistant crops: a review. *J Environ Qual* 35:1633-1658.

Cheng, M. et al. (1997). Genetic Transformation of Wheat Mediated by *Agrobacterium tumefaciens*. *Plant Physiol* 115:971-980.

Chilton, M. D. et al. (1974). *Agrobacterium tumefaciens* DNA and PS8 bacteriophage DNA not detected in crown gall tumors. *Proc Natl Acad Sci USA* 71:3672-3676.

Christou, P. (1997). Rice transformation: bombardment. *Plant Mol Biol* 35:197-203.

Christou, P. et al. (1988). Stable Transformation of Soybean Callus by DNA-Coated Gold Particles. *Plant Physiol* 87:671-674.

Christou, P. et al. (1987). Stable transformation of soybean by electroporation and root formation from transformed callus. *Proc Natl Acad Sci USA* 84:3962-3966.

de Groot, M. J. et al. (1998). *Agrobacterium tumefaciens*-mediated transformation of filamentous fungi. *Nat Biotechnol* 16:839-842.

Dunwell, J. M. (1999). Transformation of maize using silicon carbide whiskers. *Methods Mol Biol* 111:375-382.

Dunwell, J. M. (2000). Transgenic approaches to crop improvement. *J Exp Bot* 51:GMP Special Issue: 487-496.

Gould, J. et al. (1991). Transformation of *Zea mays* L. Using *Agrobacterium tumefaciens* and the Shoot. Apex. *Plant Physiol* 95:426-434.

Hansen, G. et al. (1994). Constitutive expression of the virulence genes improves the efficiency of plant transformation by *Agrobacterium*. *Proc Natl Acad Sci USA* 91:7603-7607.

Hayashimoto, A. et al. (1990). A Polyethylene Glycol-Mediated Protoplast Transformation System for Production of Fertile Transgenic Rice Plants. *Plant Physiol* 93:857-863.

Jha, T. B. et al. (2007). Somatic embryogenesis in *Jatropha curcas* Linn., an important biofuel plant. *Plant Biotechnology Reports* 1:135-140.

Lazo, G. R. et al. (1991). A DNA transformation-competent *Arabidopsis* genomic library in *Agrobacterium*. *Biotechnology* 9:963-967.

Lee, N. et al. (1991). Efficient transformation and regeneration of rice small cell groups. *Proc Natl Acad Sci USA* 88:6389-6393.

Li, M. et al. (2008). Establishment of an *Agrobacterium*-mediated cotyledon disc transformation method for *Jatropha curcas*. *Plant Cell Tiss Organ Cult* 44:173-181.

McLean, B. G. et al. (1994). Mutants of *Agrobacterium* VirA that activate vir gene expression in the absence of the inducer acetosyringone. *J Biol Chem* 269:2645-2651.

Olhoft, P. M. et al. (2003). Efficient soybean transformation using hygromycin B selection in the cotyledonary-node method. *Planta* 216:723-35.

Sagi, M. and Fluhr, R. (2001). Superoxide production by plant homologues of the gp91(phox) NADPH oxidase. Modulation of activity by calcium and by tobacco mosaic virus infection. *Plant Physiol* 126:1281-1290.

Sidorov, V. and Duncan, D. (2009). *Agrobacterium*-mediated maize transformation: immature embryos versus callus. *Methods Mol Biol* 526:47-58.

Vega, J. M. et al. (2008). Improvement of *Agrobacterium*-mediated transformation in Hi-II maize (*Zea mays*) using standard binary vectors. *Plant Cell Rep* 27:297-305.

Veluthambi, K. et al. (1989). Opines stimulate induction of the vir genes of the *Agrobacterium tumefaciens* Ti plasmid. *J Bacteriol* 171:3696-3703.

Wang, K. and Frame, B. (2009). Biolistic gun-mediated maize genetic transformation. *Methods Mol Biol* 526:29-45.

Zhang, J. et al. (1997). *Agrobacterium*-mediated transformation of elite indica and japonica rice cultivars. *Mol Biotechnol* 8:223-231.

What is claimed is:

1. *Agrobacterium tumefaciens* strain AGL2 deposited with the American Type Culture Collection under Accession Number PTA 10447.

2. *Agrobacterium tumefaciens* strain AGL3 deposited with the American Type Culture Collection under Accession Number PTA 10448.

\* \* \* \* \*